US012628828B2

(12) United States Patent
Kurata et al.

(10) Patent No.: US 12,628,828 B2
(45) Date of Patent: May 19, 2026

(54) FUNCTIONAL MATERIAL AND METHOD FOR PRODUCING SAME

(71) Applicant: HONDA MOTOR CO., LTD., Tokyo (JP)

(72) Inventors: Mayu Kurata, Tochigi (JP); Takehiro Mugishima, Tochigi (JP)

(73) Assignee: HONDA MOTOR CO., LTD., Tokyo (JP)

( * ) Notice: Subject to any disclaimer, the term of this patent is extended or adjusted under 35 U.S.C. 154(b) by 798 days.

(21) Appl. No.: 17/914,761

(22) PCT Filed: Mar. 25, 2021

(86) PCT No.: PCT/JP2021/012631
§ 371 (c)(1),
(2) Date: Sep. 27, 2022

(87) PCT Pub. No.: WO2021/193843
PCT Pub. Date: Sep. 30, 2021

(65) Prior Publication Data
US 2023/0345945 A1      Nov. 2, 2023

(30) Foreign Application Priority Data

Mar. 27, 2020   (JP) ................................. 2020-057484
Oct. 7, 2020   (JP) ................................. 2020-170093

(51) Int. Cl.
| | |
|---|---|
| *A01N 59/16* | (2006.01) |
| *A01N 25/08* | (2006.01) |
| *A01P 1/00* | (2006.01) |
| *A01P 3/00* | (2006.01) |
| *A61L 2/232* | (2006.01) |
| *A61L 101/30* | (2006.01) |

(52) U.S. Cl.
CPC ............. *A01N 59/16* (2013.01); *A01N 25/08* (2013.01); *A01P 1/00* (2021.08); *A01P 3/00* (2021.08); *A61L 2/232* (2013.01); *A61L 2101/30* (2020.08)

(58) Field of Classification Search
CPC ............... A61L 2300/404; A61L 31/16; A61L 2300/208; A61L 29/08; A61L 29/085; A61L 29/16; A61L 31/08; A61L 31/10; A61L 2/00; A61L 2/03; A61L 2/232; A61L 2/238; A61L 2/26; A61L 2101/30; A61L 2300/102; A61L 2300/104; A61L 2300/108; A61L 2400/12; A61L 2420/02; A61L 2420/06; A61L 27/04; A61L 27/06; A61L 27/08; A61L 27/30; A61L 27/303; A61L 27/306; A61L 27/50; A61L 27/54; A61L 31/022; A61L 31/082; A61L 31/084; A61L 31/14; C23C 22/63; C23C 22/60; C23C 24/08; C23C 26/00
See application file for complete search history.

(56) References Cited

U.S. PATENT DOCUMENTS

| | | | |
|---|---|---|---|
| 2012/0088860 A1 | 4/2012 | Wissemborski et al. | |
| 2012/0293740 A1 | 11/2012 | Sudo | |
| 2017/0227305 A1* | 8/2017 | Yamada .................. | F28F 19/02 |
| 2021/0206136 A1 | 7/2021 | Murata et al. | |

FOREIGN PATENT DOCUMENTS

| | | |
|---|---|---|
| CN | 101243206 A | 8/2008 |
| EP | 1930473 A1 | 6/2008 |
| JP | H11124697 A | 5/1999 |
| JP | H11200064 A | 7/1999 |
| JP | 2017503554 A | 2/2017 |
| JP | 6411962 B2 | 10/2018 |
| JP | 2019506535 A | 3/2019 |
| JP | 2021037226 A | 3/2021 |
| WO | 2015031956 A1 | 3/2015 |
| WO | 2016021367 A1 | 2/2016 |
| WO | 2017138890 A1 | 8/2017 |
| WO | 2020067500 A1 | 4/2020 |

OTHER PUBLICATIONS

EP3413710A1 translation (Year: 2018).*
Office Action issued in the CN Patent Application No. 202180023619.2, mailed on Mar. 6, 2024.
Kojima, Ryuji et al. "Fundamental Characteristics of Zinc Phosphate Coating" Tetsu-to-Hagane, 1. Introduction, 2. Crystal Condition of Film, Jun. 1, 1980, vol. 66, No. 7, pp. 924-934.

* cited by examiner

*Primary Examiner* — Audrea B Coniglio
(74) *Attorney, Agent, or Firm* — CKC & Partners Co., LLC

(57) ABSTRACT

A functional material has a metal substrate and exhibits at least one of the following: an antimold action, an antimicrobial action, and an antiviral action. The functional material is provided with: a metal substrate produced by forming a zinc layer on the surface of an aluminum substrate; and a functional film that is a zinc phosphate film formed on the surface of the metal substrate. A micron-order unevenness is formed on the surface of the functional film, as a result of which the functional film has at least one of the following: an antimold action that prevents the proliferation of mold, an antimicrobial action that kills microorganisms, and an antiviral action that inactivates viruses. The functional material is produced by carrying out a zinc phosphate chemical conversion treatment on the surface of an aluminum substrate and forming on this surface a zinc phosphate film having micron-order unevenness.

14 Claims, 10 Drawing Sheets

FIG. 3

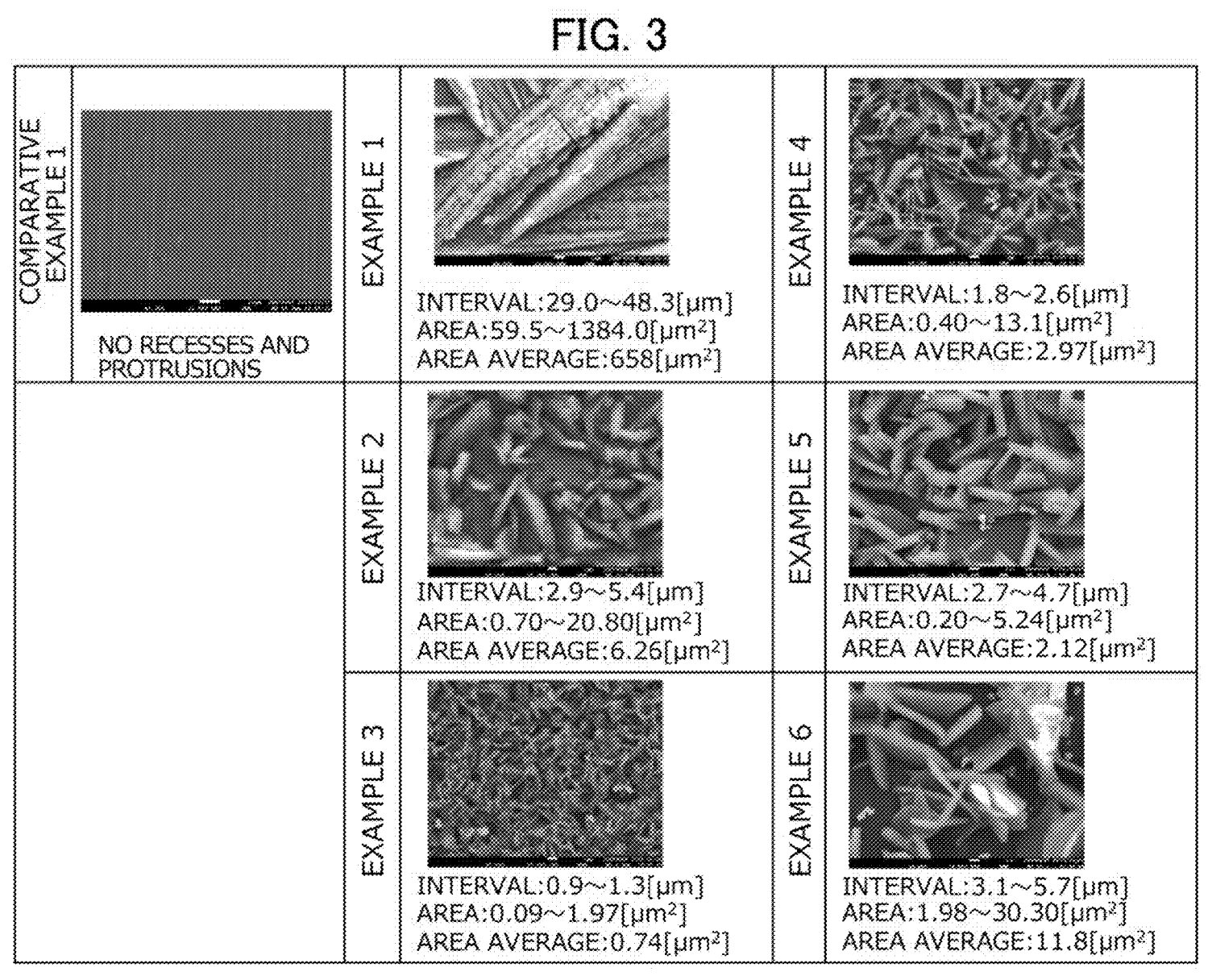

EXAMPLE 1
INTERVAL:29.0~48.3[μm]
AREA:59.5~1384.0[μm²]
AREA AVERAGE:658[μm²]

EXAMPLE 2
INTERVAL:2.9~5.4[μm]
AREA:0.70~20.80[μm²]
AREA AVERAGE:6.26[μm²]

EXAMPLE 3
INTERVAL:0.9~1.3[μm]
AREA:0.09~1.97[μm²]
AREA AVERAGE:0.74[μm²]

EXAMPLE 4
INTERVAL:1.8~2.6[μm]
AREA:0.40~13.1[μm²]
AREA AVERAGE:2.97[μm²]

EXAMPLE 5
INTERVAL:2.7~4.7[μm]
AREA:0.20~5.24[μm²]
AREA AVERAGE:2.12[μm²]

EXAMPLE 6
INTERVAL:3.1~5.7[μm]
AREA:1.98~30.30[μm²]
AREA AVERAGE:11.8[μm²]

COMPARATIVE EXAMPLE 1
NO RECESSES AND PROTRUSIONS

FIG. 5

| | | COMPARATIVE EXAMPLE 1 | EXAMPLE 1 | EXAMPLE 2 | EXAMPLE 3 | EXAMPLE 4 | EXAMPLE 5 | EXAMPLE 6 |
|---|---|---|---|---|---|---|---|---|
| FIRST STERILIZATION TEST | 0 HOUR | 4.29 | 4.27 | 4.29 | 4.23 | 4.23 | 4.23 | 4.23 |
| | 24 HOURS | 2.53 | 2.50 | <-0.20 | <-0.20 | <-0.20 | <-0.20 | <-0.20 |
| SECOND STERILIZATION TEST | 0 HOUR | 4.25 | 4.23 | 4.24 | 4.11 | 4.11 | 4.11 | 4.11 |
| | 24 HOURS | 1.97 | 1.94 | <-0.20 | <-0.20 | <-0.20 | <-0.20 | <-0.20 |
| ANTIFUNGAL TEST | | 4 | 0 | 0 | 2 | 2 | 0 | 0 |

FIG. 8A

| TESTING OPERATION | DEVAICE USED | TIME (MINUTE) | | | | | | |
|---|---|---|---|---|---|---|---|---|
| | | 0    15 | 30 | 45 | 60 | 90 | 180 | |
| HOMOGENIZATION OF AIR IN TEST CHAMBER | AGITATING FAN | → | | | | | | |
| SPRAYING OF TEST VIRUS | VIRUS SPRAYER | 10MIN → ● AGITATING FOR 2 MIN | | | | | | |
| COLLECTION OF FLOATING VIRUSES | FLOATING VIRUS COLLECTOR | 2MIN → | 2MIN → | 2MIN → | 2MIN → | 2MIN → | 2MIN → | 2MIN → |

FIG. 8B

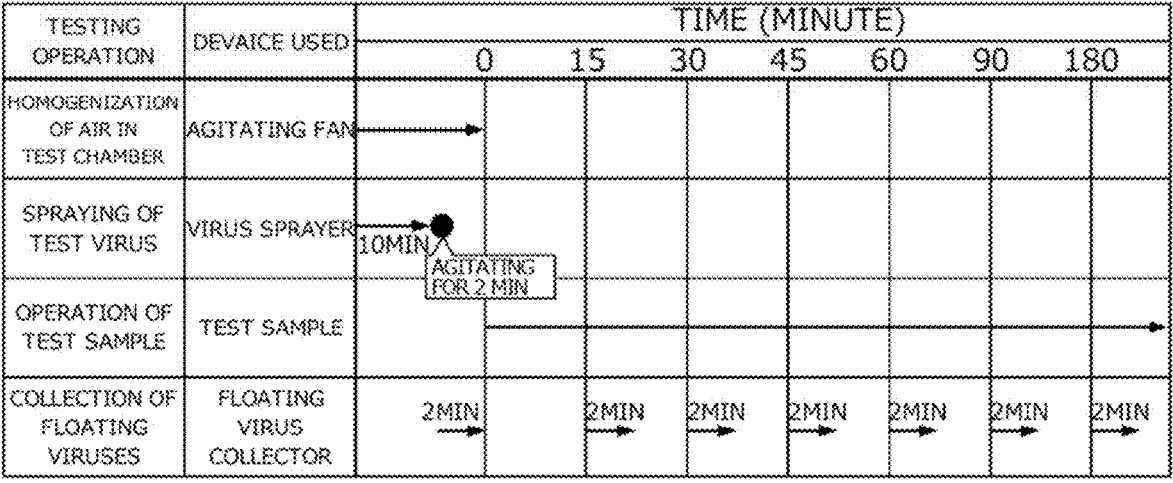

| TESTING OPERATION | DEVAICE USED | TIME (MINUTE) | | | | | | |
|---|---|---|---|---|---|---|---|---|
| | | 0    15 | 30 | 45 | 60 | 90 | 180 | |
| HOMOGENIZATION OF AIR IN TEST CHAMBER | AGITATING FAN | → | | | | | | |
| SPRAYING OF TEST VIRUS | VIRUS SPRAYER | 10MIN → ● AGITATING FOR 2 MIN | | | | | | |
| OPERATION OF TEST SAMPLE | TEST SAMPLE | →――――――――――――――――――――→ | | | | | | |
| COLLECTION OF FLOATING VIRUSES | FLOATING VIRUS COLLECTOR | 2MIN → | 2MIN → | 2MIN → | 2MIN → | 2MIN → | 2MIN → | 2MIN → |

FUNCTIONAL MATERIAL AND METHOD FOR PRODUCING SAME

TECHNICAL FIELD

The present invention relates to a functional material and a method for producing the same. More specifically, the present invention relates to a functional material having an antifungal effect to prevent the growth of mold and a bactericidal effect to kill microorganisms (e.g., bacteria), and the like, and a method for producing the same.

BACKGROUND ART

It is known that fine structures of nano-order recesses and protrusions, such as wings of dragonflies or cicadas and black silicon, have a bactericidal effect to kill bacteria. In recent years, functional materials having a bactericidal effect have been actively developed based on such a finding.

For example, Patent Document 1 discloses an invention relating to a synthetic polymer film having a bactericidal effect. A plurality of nanopillars is formed on the surface of the synthetic polymer film disclosed in Patent Document 1, and the width of these nanopillars is in a range of 20 [nm] to 500 [nm].

Patent Document 1: Japanese Patent No. 6411962

DISCLOSURE OF THE INVENTION

Problems to be Solved by the Invention

As described above, the functional material disclosed in Patent Document 1 is assumed to be prepared by using a resin material as a base material, and the use of a metal material, such as aluminum or zinc, as a base material by imparting a bactericidal effect to the surface thereof has not been sufficiently studied.

An object of the present invention is to provide a functional material which is prepared by using metal as a base material and has at least one selected from an antifungal effect, a bactericidal effect, and an antiviral action; and a method for producing the same.

Means for Solving the Problems (1) A functional material according to the present invention (e.g., a functional material 1 described later) includes a metal base material (e.g., a metal base material 2 described later) and a zinc phosphate film (e.g., a functional film 3 described later) formed on a surface of the metal base material (e.g., a zinc layer 25 described later). The functional material has micron-order recesses and protrusions formed on the zinc phosphate film, and has at least one selected from an antifungal effect, a bactericidal effect, and an antiviral action.

(2) In this case, an interval between protrusions formed on the zinc phosphate film is preferably in a range of 0.5 [μm] to 50.0 [μm].

(3) In this case, it is preferable that the interval between protrusions is in a range of 0.5 [μm] to 6.0 [μm] and the functional material has a bactericidal effect.

(4) In this case, it is preferable that the interval between protrusions is in a range of 2.7 [μm] to 50.0 [μm] and the functional material has an antifungal effect.

(5) In this case, it is preferable that the interval between protrusions is in a range of 0.5 [μm] to 1.5 [μm] and the functional material has an antiviral action.

(6) In this case, a recess formed on the zinc phosphate film preferably has an area in a range of 0.05 [μm$^2$] to 1,400 [μm$^2$].

(7) In this case, it is preferable that the area of the recess is in a range of 0.05 [μm$^2$] to 31.0 [μm$^2$] and the functional material has a bactericidal effect.

(8) In this case, it is preferable that the area of a recess is in a range of 0.05 [μm$^2$] to 2.0 [μm$^2$] and the functional material has an antiviral action.

(9) A functional material having at least one selected from an antifungal effect, a bactericidal effect, and an antiviral action according to the present invention is characterized by being obtained by subjecting a metal base material to a zinc phosphate chemical conversion treatment to form a zinc phosphate film having micron-order recesses and protrusions on a surface of the metal base material.

Effects of the Invention (1) The functional material according to the present invention includes a metal base material and a zinc phosphate film formed on the surface of this metal base material, and micron-order (specifically, about 1 [μm] to about 1,000 [μm]) recesses and protrusions are formed on this zinc phosphate film. The present invention can make at least one selected from an antifungal effect, a bactericidal effect, and an antiviral action stronger than the metal base material having no micron-order recesses and protrusions as described above.

(2) The functional material according to the present invention can impart a stronger antifungal effect by having an interval between protrusions formed on the zinc phosphate film in a range of 0.5 [μm] to 50.0 [μm].

(3) The functional material according to the present invention can impart a bactericidal effect in addition to a stronger antifungal effect by having an interval between protrusions formed on the zinc phosphate film in a range of 0.5 [μm] to 6.0 [μm].

(4) The functional material according to the present invention can impart a stronger antifungal effect by having an interval between protrusions formed on the zinc phosphate film in a range of 2.7 [μm] to 50.0 [μm].

(5) The functional material according to the present invention can impart an antiviral action that inactivates viruses by having an interval between protrusions formed on the zinc phosphate film in a range of 0.5 [μm] to 1.5 [μm].

(6) The functional material according to the present invention can impart a stronger antifungal effect by having an area of a recess formed on the zinc phosphate film in a range of 0.05 [μm$^2$] to 1,400 [μm$^2$].

(7) The functional material according to the present invention can impart a bactericidal effect in addition to a stronger antifungal effect by having an area of the recess formed on the zinc phosphate film in a range of 0.05 [μm$^2$] to 31.0 [μm$^2$].

(8) The functional material according to the present invention can impart an antiviral action by having an area of the recess formed on the zinc phosphate film in a range of 0.05 [μm$^2$] to 2.0 [μm$^2$].

(9) A method for producing a functional material having at least one selected from an antifungal effect, a bactericidal effect, and an antiviral action according to the present invention includes subjecting a metal base material to a zinc phosphate chemical conversion treatment to form a zinc phosphate film having micron-order recesses and protrusions on the surface of the metal base material. This enables the formation of a zinc phosphate film having at least one selected from an antifungal effect, a bactericidal effect, and an antiviral action on the surface of the metal base material in a simple procedure.

BRIEF DESCRIPTION OF THE DRAWINGS

FIG. 3 shows SEM images of surfaces of functional films in Comparative Example 1 and Examples 1 to 6 as observed by a scanning electron microscope;

FIG. 5 shows results of first sterilization tests, second sterilization tests, and antifungal tests for Comparative Example 1 and Examples 1 to 6;

FIG. 8A is a test process chart showing a procedure for evaluating the natural attenuation of floating viruses;

FIG. 8B is a test process chart showing a procedure for evaluating the suppression performance of floating viruses by a test sample;

PREFERRED MODE FOR CARRYING OUT THE INVENTION

First Embodiment

Hereinafter, a functional material according to the first embodiment of the present invention and a method for producing the same will be described with reference to the drawings.

Figure 1:
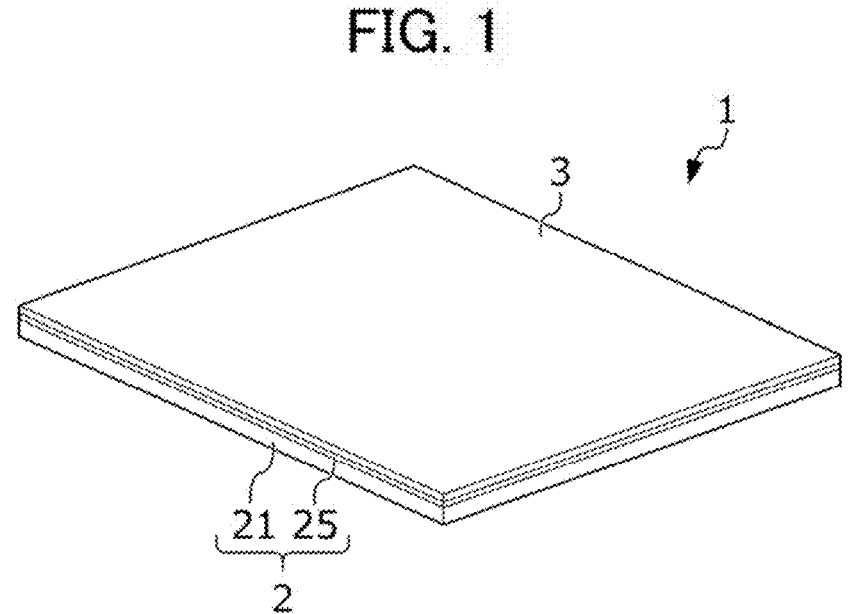
FIG. 1 is a perspective view illustrating a configuration of a functional material according to the first embodiment of the present invention.

FIG. 1 is a perspective view illustrating a configuration of a functional material 1 according to the present embodiment. The functional material 1 includes a flat metal base material 2 and a functional film 3 formed on the surface of this metal base material 2.

The metal base material 2 includes an aluminum base material 21 and a zinc layer 25 formed on the surface of this aluminum base material 21. Note that FIG. 1 illustrates a case in which the metal base material 2 is the aluminum base material 21 with the zinc layer 25 formed on its surface, but the present invention is not limited thereto. The metal base material 2 may be the aluminum base material 21 without the zinc layer 25 formed on its surface.

The aluminum base material 21 is a flat plate material composed of aluminum or an aluminum alloy containing copper, manganese, silicon, magnesium, zinc, nickel, or the like with aluminum as a main component. Note that the aluminum base material 21 is described below as the flat plate material composed of aluminum of the aluminum alloy, but the present invention is not limited thereto. The shape of the aluminum base material 21 is not limited to a flat plate but may be any shape that suits its application.

The zinc layer 25 is a film composed mainly of zinc formed on the surface of the aluminum base material 21. The zinc layer 25 is formed, for example, by subjecting the aluminum base material 21 to a known zinc plating treatment.

The functional film 3 is formed on the surface of the metal base material 2, i.e., the surface of the zinc layer 25. The functional film 3 is a zinc phosphate film, and numerous micron-order (specifically, in the range of 1 [μm] to 1,000 [μm]) recesses and protrusions in fine and irregular shapes are formed on the surface thereof. The numerous protrusions formed on the functional film 3 are blade-shaped, and their orientations in planar view are irregular. On the functional film 3, numerous recesses are formed as a concave space defined by a plurality of these protrusions. The interval between the adjacent protrusions in planar view, in other words, the length of one side of the recess in planar view is of micron-order. As will be described in detail later, the functional film 3 has a bactericidal effect to kill microorganisms (e.g., bacteria) depending on the interval between the protrusions, in addition to an antifungal effect to prevent the growth of mold.

Note that FIG. 1 illustrates a case in which the metal base material 2 is the aluminum base material 21 with the zinc layer 25 formed on its surface, and the functional film 3 is formed on the surface of this metal base material 2, i.e., the surface of the zinc layer 25, but the present invention is not limited thereto. As described later in Examples 3 to 8, the functional film may be formed directly on the surface of the aluminum base material.

Note that in the present invention, the function of killing bacteria is referred to as a bactericidal effect, the function of preventing the growth of mold is referred to as an antifungal effect, and the function of inactivating viruses is referred to as an antiviral action. Hereafter, the functional material having a stronger bactericidal effect when compared to a material of Comparative Example 1 described later is also referred to as a bactericidal material. The functional material having a stronger antifungal effect when compared to the material of Comparative Example 1 is also referred to as an antifungal material. In addition, the functional material having stronger bactericidal and antifungal effects when compared to the material of Comparative Example 1 is also referred to as a bactericidal/antifungal material. The functional material having a stronger antiviral action when compared to the material of Comparative Example 1 is also referred to as an antiviral material.

Figure 2:
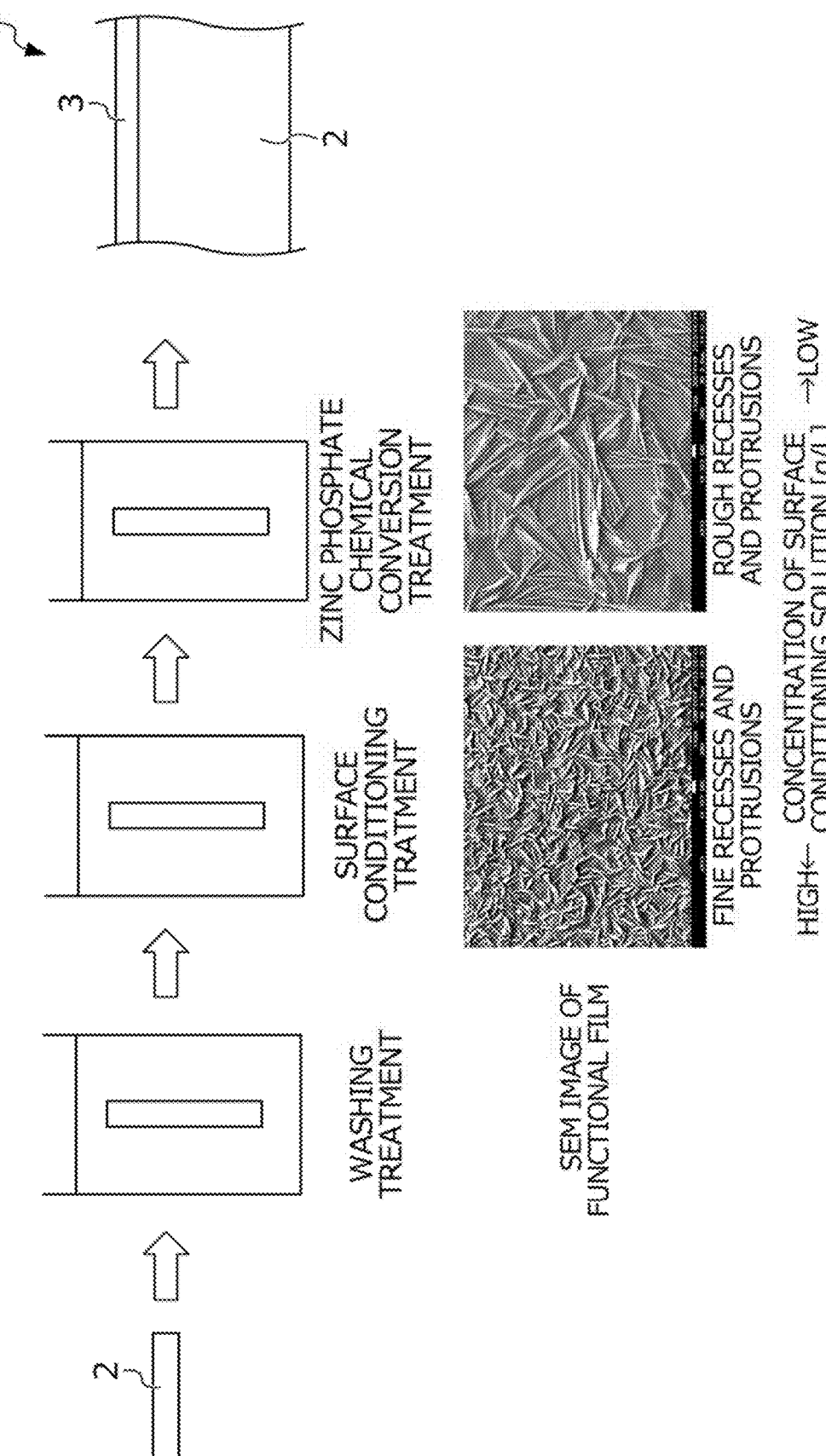
FIG. 2 is a diagram illustrating steps of producing a functional material.

FIG. 2 is a diagram illustrating steps of producing a functional material 1. As illustrated in FIG. 2, the functional material 1 is produced by carrying out zinc plating, washing, and zinc phosphate chemical conversion treatments. More specifically, the steps of producing the functional material 1 includes: preparing an aluminum base material 21 as a raw material; producing a metal base material 2 by subjecting the prepared aluminum base material 21 to a known zinc plating treatment (e.g., an electrolytic zinc plating treatment) to form a zinc layer 25 on the surface of the aluminum base material 21; washing, degreasing, and rinsing this metal base material 2; performing a surface conditioning process in which the washed metal base material 2 is immersed in a surface conditioning solution to attach nuclei that trigger crystals onto the surface thereof; and forming a functional film 3 as a zinc phosphate film having micron-order recesses and protrusions on the surface of the zinc layer 25 by subjecting the metal base material 2 that has undergone the surface conditioning process to a zinc phosphate chemical conversion treatment in contact with a zinc phosphate treatment solution for a predetermined time. As illustrated in the lower row of FIG. 2, recesses and protrusions formed on the functional film 3 can be varied from rough to fine by changing the concentration of the surface conditioning solution used in the surface conditioning process. The aluminum base material with the functional film directly formed on its surface, as in Examples 3 to 8 described later, is produced without the above zinc plating treatment by washing, degreasing, and rinsing the metal base material (aluminum base material) 21; performing the surface conditioning process in which the washed metal base material 2 is immersed in the surface conditioning solution to attach nuclei that trigger crystals onto the surface thereof; and forming the functional film 3 as a zinc phosphate film having micron-order recesses and protrusions on the surface of the metal base material 2 by subjecting the metal base material 2 that has undergone the surface conditioning process to the zinc phosphate chemical conversion treatment in contact with the zinc phosphate treatment solution for a predetermined time. Note that the functional film 3 formed on the surface of the metal base material 2 through the above-mentioned production process could not be peeled off at least by hand. The lower row of FIG. 2 shows an example of SEM images of the surfaces of the functional film 3 taken by a scanning electron microscopy. More specifically, the lower row of FIG. 2 shows SEM images of the surfaces of the functional film 3 in the case of applying the zinc phosphate chemical conversion treatment using different concentrations of the surface conditioning solution. As illustrated in FIG. 2, recesses and protrusions formed on the functional film 3 tend to become fine as the concentration of the surface conditioning solution is increased.

Next, the contents of first and second sterilization tests and antifungal tests conducted to verify the bactericidal and antifungal effects of the functional material 1 according to the present embodiment will be described, as well as Comparative Example 1 and Examples 1 to 6 used in these tests.

FIG. 3 shows SEM images of the surfaces of the functional films in Comparative Example 1 and Examples 1 to 6 taken under magnification by a scanning electron microscopy. FIG. 3 also shows the minimum and maximum values of the interval [μm] between adjacent portions in a plurality of protrusions formed on the surfaces of functional films along with the magnification of each SEM image.

Figure 4:
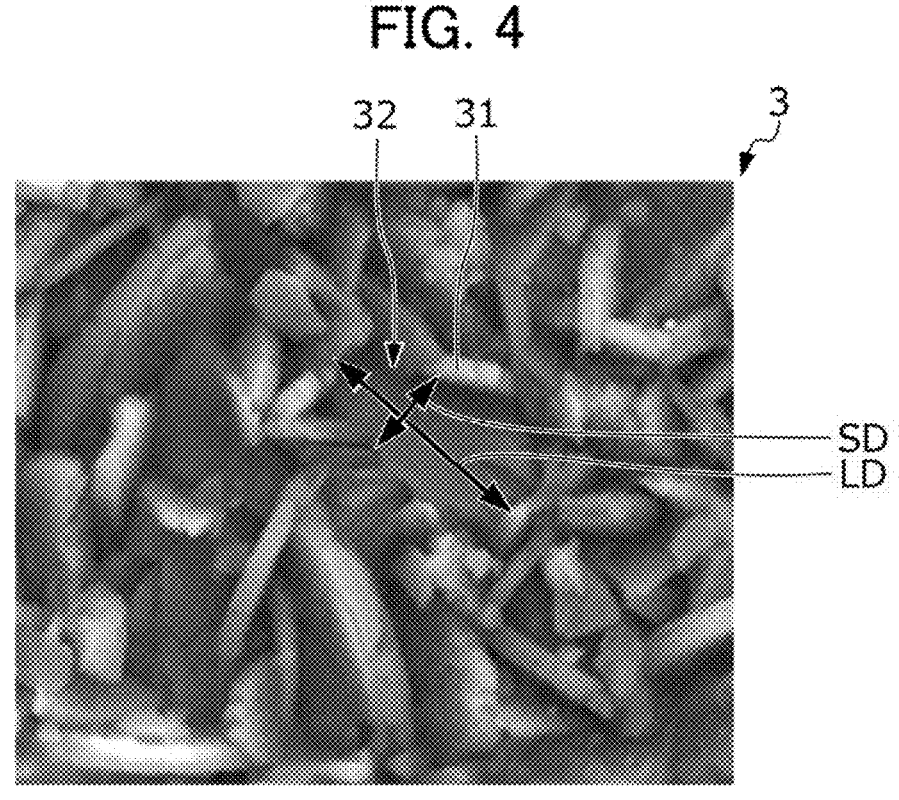
FIG. 4 is a view for describing a procedure of calculating an interval between adjacent protrusions.

FIG. 4 is a view for describing a procedure of calculating the interval between adjacent protrusions. As shown in FIG. 4, numerous blade-shaped protrusions 31 (portions seen brightly in FIG. 4) with irregular orientations are formed on the surface of the functional film 3. Therefore, on the surface of the functional film 3, numerous recesses 32 (portions seen dark in FIG. 4) are formed as a concave space defined by a plurality of these protrusions 31.

In the present invention, the length of one side of the recesses 32 in planar view is defined as an interval between the adjacent protrusions 31 in planar view. More specifically, the shape of each recess 32 formed on the surface of the functional film 3 in planar view is regarded as a shape capable of defining a longitudinal direction LD and a shorter direction SD orthogonal thereto (e.g., a rectangular shape or an elliptical shape), the longitudinal direction LD and the shorter direction SD orthogonal thereto are defined for the recesses 32, and the lengths of the recesses 32 along the longitudinal direction LD and the shorter direction SD are defined as the interval between the adjacent protrusions 31. The length of each recess 32 along the longitudinal direction LD and the shorter direction SD is calculated based on the above definitions, and the minimum length along the shorter direction SD is the minimum interval between the protrusions 31 while the maximum length along the longitudinal direction LD is the maximum interval between the protrusions 31.

<Comparative Example 1>

In the above tests, an aluminum base material that had not been subjected to the zinc plating or zinc phosphate chemical conversion treatment as described above was designated as Comparative Example 1. A1000 series was also used as the aluminum base material. As shown in FIG. 3, since a functional material of Comparative Example 1 has not undergone a zinc plating or zinc phosphate chemical conversion treatment, the surface thereof is substantially flat and has no recesses and protrusions.

<Example 1>

In the above tests, the functional material produced through the production process was described with reference to FIG. 2, using the same aluminum base material (i.e., A1000 series) as that used in Comparative Example 1, as the material and designated as Example 1. More specifically, in Example 1, "Ferricoat 7" manufactured by Nihon Parkerizing Co., Ltd. was used as a zinc phosphate treatment solution. As shown in FIG. 3, an interval between protrusions formed on a functional film in Example 1 was in a range of 29.0 [μm] to 48.3 [μm]. An area of a recess was in a range of 59.5 [μm$^2$] to 1384.0 [μm$^2$]. The average area of the recess was 658 [μm$^2$].

<Example 2>

In the above tests, the functional material produced through the production process described with reference to FIG. 2, using the same aluminum base material (i.e., A1000 series) as that used in Comparative Example 1, as the material was designated as Example 2. More specifically, in Example 2, "Palbond 880" manufactured by Nihon Parkerizing Co., Ltd. was used as a zinc phosphate treatment solution. That is, Example 1 and Example 2 differ in components of the zinc phosphate treatment solution. As shown in FIG. 3, an interval between protrusions formed on a functional film in Example 2 was in a range of 2.9 [μm] to 5.4 [μm]. That is, the interval of the protrusions formed on the functional film of Example 2 is shorter than the interval of the protrusions formed on the functional film of Example 1, and the variation of the interval is also smaller. An area of a recess was in a range of 0.70 [μm$^2$] to 20.80 [μm$^2$]. The average area of the recess was 6.26 [μm$^2$].

<Example 3>

In the above test, the same aluminum base material (i.e., A1000 series) was used in Comparative Example 1 as a material, and the functional material produced by directly subjecting this aluminum base material to the zinc phosphate chemical conversion treatment without the zinc plating treatment shown in FIG. 2 was designated as Example 3. More specifically, in Example 3, "PB-LA37L" manufactured by Nihon Parkerizing Co., Ltd. was used as a zinc phosphate treatment solution. That is, Example 3 differs from Examples 1 and 2 in terms of the lack of the zinc plating treatment and components of the zinc phosphate treatment solution. The concentration of the surface conditioning solution use in the surface conditioning process was 3 g/L. As shown in FIG. 3, an interval between protrusions formed on a functional film in Example 3 was in a range of 0.9 [μm] to 1.3 [μm]. That is, the interval of the protrusions formed on the functional film of Example 3 is shorter than the Interval of the protrusions formed on the functional film of Example 1, and the variation of the interval is also smaller. An area of a recess was in a range of 0.09 [μm²] to 1.97 [μm²]. The average area of the recess was 0.74 [μm²].

<Example 4>

In the above test, the same aluminum base material (i.e., A1000 series) was used in Comparative Example 1 as a material, and the functional material produced by directly subjecting this aluminum base material to the zinc phosphate chemical conversion treatment without the zinc plating treatment shown in FIG. 2 was designated as Example 4. More specifically, in Example 4, "PB-LA37L" manufactured by Nihon Parkerizing Co., Ltd. was used as a zinc phosphate treatment solution. That is, Example 4 and Example 3 have the same components in the zinc phosphate treatment solution. The concentration of the surface conditioning solution used in the surface conditioning process was also 1 g/L, which is lower than the concentration in Example 3, and the crystal size was larger than in Example 3. As shown in FIG. 3, an interval between protrusions formed on a functional film in Example 4 was in a range of 1.8 [μm] to 2.6 [μm]. That is, the interval of the protrusions formed on the functional film of Example 4 is longer than the interval of the protrusions formed on the functional film of Example 2, and the variation of the interval is also large. An area of a recess was in a range of 0.40 [μm²] to 13.1 [μm²]. The average area of the recess was 2.97 [μm²].

<Example 5>

In the above test, the same aluminum base material (i.e., A1000 series) was used in Comparative Example 1 as a material, and the functional material produced by directly subjecting this aluminum base material to the zinc phosphate chemical conversion treatment without the zinc plating treatment shown in FIG. 2 was designated as Example 5. More specifically, in Example 5, "PB-LA37L" manufactured by Nihon Parkerizing Co., Ltd. was used as a zinc phosphate treatment solution. That is, Example 5 and Examples 3 and 4 have the same components in the zinc phosphate treatment solution. The concentration of the surface conditioning solution used in the surface conditioning process was also 1 g/L, the same as in Example 4, and the crystal size was further increased by carrying out a chemical conversion treatment under conditions of increased film components in the chemical conversion treatment. As shown in FIG. 3, an interval between protrusions formed on a functional film in Example 5 was in a range of 2.7 [μm] to 4.7 [μm]. That is, the interval of the protrusions formed on the functional film of Example 5 is longer than the interval of the protrusions formed on the functional film of Example 4, and the variation of the interval is also large. An area of a recess was in a range of 0.20 [μm²] to 5.24 [μm²]. The average area of the recess was 2.12 [μm²].

<Example 6>

In the above test, the same aluminum base material (i.e., A1000 series) was used in Comparative Example 1 as a material, and the functional material produced by directly subjecting this aluminum base material to the zinc phosphate chemical conversion treatment without the zinc plating treatment shown in FIG. 2 was designated as Example 6. More specifically, in Example 6, "PB-LA37" manufactured by Nihon Parkerizing Co., Ltd. was used as a zinc phosphate treatment solution. That is, Example 6 and Examples 3 to 5 have the same components in the zinc phosphate treatment solution. The concentration of the surface conditioning solution used in the surface conditioning process was also 1 g/L, the same as in Examples 4 and 5, and the crystal size was further increased by carrying out a chemical conversion treatment under conditions of increased film components in the chemical conversion treatment. As shown in FIG. 3, an interval between protrusions formed on a functional film in Example 6 was in a range of 3.1 [μm] to 5.7 [μm]. That is, the interval of the protrusions formed on the functional film of Example 6 is longer than the interval of the protrusions formed on the functional film of Example 5, and the variation of the interval is also large. An area of a recess was in a range of 1.98 [μm²] to 30.3 [μm²]. The average area of the recess was 11.8 [μm²].

First Sterilization Test

In first sterilization tests, the function of killing *Escherichia coli*, a gram-negative bacterium, was verified for Comparative Example 1 and Examples 1 to 6. More specifically, the bactericidal effect of the functional materials of Comparative Example 1 and Examples 1 to 6 on *Escherichia coli*, further specifically, the number of viable bacteria (cells/cm²) after a lapse of 24 hours from the dropwise addition of the bacterial cells onto the functional film, was measured in accordance with JIS 2801.

FIG. 5 shows results of the first sterilization tests, second sterilization tests described later, and antifungal tests described later. As shown in FIG. 5, the common logarithm of the number of viable bacteria after 0 hours was 4.29 in Comparative Example 1, and the common logarithm of the number of viable bacteria after 24 hours was 2.53. The common logarithm of the number of viable bacteria after 0 hours was 4.27 in Example 1, and the common logarithm of the number of viable bacteria after 24 hours was 2.50. The common logarithm of the number of viable bacteria after 0 hours was 4.29 in Example 2, and the common logarithm of the number of viable bacteria after 24 hours was the detection limit (−0.20) or less. The common logarithm of the number of viable bacteria after 0 hours was 4.23 in Example 3, and the common logarithm of the number of viable bacteria after 24 hours was the detection limit (−0.20) or less. The common logarithm of the number of viable bacteria after 0 hours was 4.23 in Example 4, and the common logarithm of the number of viable bacteria after 24 hours was the detection limit (−0.20) or less. The common logarithm of the number of viable bacteria after 0 hours was 4.23 in Example 5, and the common logarithm of the number of viable bacteria after 24 hours was the detection limit (−0.20) or less. The common logarithm of the number of viable bacteria after 0 hours was 4.23 in Example 6, and the common logarithm of the number of viable bacteria after 24 hours was the detection limit (−0.20) or less. Therefore, it was verified that the functional materials of Examples 2 to 6 have a stronger bactericidal effect than the functional material if Comparative Example 1, and can be used as a bactericidal material with bactericidal effect against *Escherichia coli*, a gram-negative bacterium.

Note that none of the functional films of Examples 1 to 6 peeled off after the antiviral tests. Therefore, it was also Verified that the functional films, the zinc phosphate films, in the functional materials of Examples 1 to 6 each have sufficient strength.

Second Sterilization Test

In the second sterilization test, the function of killing *Staphylococcus aureus*, a gram-positive bacterium, was verified for Comparative Example 1 and Examples 1 to 6.

More specifically, the bactericidal effect of the functional materials of Comparative Example 1 and Examples 1 to 6 on *Staphylococcus aureus*, further specifically, the number of viable bacteria (cells/cm$^2$) after a lapse of 24 hours from the dropwise addition of the bacterial cells onto the functional film, was measured in accordance with JIS 2801.

As shown in FIG. 5, the results of the second sterilization test showed that the common logarithm of the number of viable bacteria after 0 hours was 4.25 in Comparative Example 1, while the common logarithm of the number of viable bacteria after 24 hours was 1.97. The common logarithm of the number of viable bacteria after 0 hours was 4.23 in Example 1, while the common logarithm of the number of viable bacteria after 24 hours was 1.94. The common logarithm of the number of viable bacteria after 0 hours was 4.24 in Example 2, while the common logarithm of the number of viable bacteria after 24 hours was the detection limit (−0.20) or less. The common logarithm of the number of viable bacteria after 0 hours was 4.11 in Example 3, while the common logarithm of the number of viable bacteria after 24 hours was the detection limit (−0.20) or less. The common logarithm of the number of viable bacteria after 0 hours was 4.11 in Example 4, while the common logarithm of the number of viable bacteria after 24 hours was the detection limit (−0.20) or less. The common logarithm of the number of viable bacteria after 0 hours was 4.11 in Example 5, while the common logarithm of the number of viable bacteria after 24 hours was the detection limit (−0.20) or less. The common logarithm of the number of viable bacteria after 0 hours was 4.11 in Example 6, while the common logarithm of the number of viable bacteria after 24 hours was the detection limit (−0.20) or less. Thus, it was verified that the functional materials of Examples 2 to 6 have a stronger bactericidal effect than the functional material of Comparative Example 1, and can be used as a bactericidal material with strong bactericidal effect against *Staphylococcus aureus*, a gram-positive bacterium.

Antifungal Test

In antifungal tests, the function of preventing the growth of six types of *Aspergillus niger* was verified for Comparative Example 1 and Examples 1 to 6. More specifically, a spore suspension of six types of mold spores, further specifically, *Aspergillus niger* NBRC 105649, *Penicillium pinophilum* NBRC 100533, *Paecilomyces variotii* NBRC 107725, *Trichoderma virens* NBRC 6355, *Chaetomium globosum* NBRC 6347, and *Cladosporium sphaerospermum* NBRC 6348 was prepared so as to have a predetermined concentration, and this spore suspension was cultured on the surfaces of the functional films for 4 weeks to measure at the predetermined intervals whether mycelial growth was visually or microscopically observed in accordance with JIS 2911. Note that in FIG. 5, if no mold growth was observed with the naked eye and under a microscope, the growth state was 0; if no mold growth was observed with the naked eye but clearly visible under a stereomicroscope, the growth state was 1; if mold growth was observed by the naked eye and the area of the growth portion was less than 25% of the total area of the specimen, the growth status was 2; if mold growth was observed by the naked eye and the area of the growth portion was 25% or more and less than 50% of the total area of the specimen, the growth status was 3; if the mycelium grew well and the area of the growth portion was 50% or more of the total area of the specimen, the growth status was 4; and if the mycelial growth was intense and covered the entire area of the specimen, the growth status was 5.

As shown in FIG. 5, the mold growth state was 4 in Comparative Example 1, 2 in Examples 3 and 4, and 0 in Examples 1, 2, 5, and 6. Therefore, it was verified that the functional materials of Examples 1 to 6 can be used as an antifungal material having a stronger antifungal effect than the functional material of Comparative Example 1. It was also verified that the functional materials of Examples 1, 2, 5, and 6 have a particularly stronger antifungal effect than the functional material of Comparative Example 1.

Second Embodiment

Next, a functional material and a method for producing the same according to the second embodiment of the present invention will be described with reference to the drawings.

The shape of the functional material according to the present embodiment differs from that of the functional material of the first embodiment described with reference to FIG. 1 or the like. That is, the shape of the functional material 1 according to the first embodiment is flat, while the shape of the functional material according to the present embodiment is fibrous and can be used as a filter. More specifically, the first embodiment describes a case in which the functional material 1 is a flat metal substrate 2 with a functional film 3, a zinc phosphate film, formed on its surface. In contrast, the present embodiment differs from the first embodiment in terms of using a fibrous metal base material, more specifically, a nonwoven fabric of aluminum fibers, as the metal base material and forming a functional film on the surface of the fibers constituting this metal base material. Note that a specific procedure for the zinc phosphate chemical conversion treatment to form a functional film (i.e., a zinc phosphate film with numerous micron-order recesses and protrusions in fine and irregular shapes) on the surface of such a fibrous metal base material is the same as in the first embodiment, so a detailed description will be omitted.

The functional film, a zinc phosphate film formed on the surface of the fibers constituting the functional material as described below, has an antiviral action that inactivates viruses floating in the air, in addition to the same antifungal and bactericidal effects as in the first embodiment.

Next, the contents of floating virus suppression performance tests conducted to verify the antiviral action of the fibrous functional materials according to the present embodiment and Examples 7 and 8 will be described.
<Example 7>

In the above evaluation test of floating virus control performance, the functional material was produced by using a nonwoven fabric of the aluminum fiber with a fiber thickness of 20 [μm] as the aluminum base material and directly subjecting this aluminum base material to a zinc phosphate chemical conversion treatment in the same procedure as in Example 3 as described above, without the zinc plating treatment shown in FIG. 2 and designated as Example 7. Since the functional material of Example 7 forms the functional film in the same procedure as that of Example 3, the interval between the protrusions formed on the functional film of Example 7, the area of the recess, and the average area of the recess are each approximately the same as those of Example 3. Therefore, the interval between the protrusions formed on the functional film of Example 7 is at least in the range of 0.5 [μm] to 1.5 [μm], and the area of the recess is at least in the range of 0.05 [μm²] to 2.0 [μm²].

<Example 8>

In the above evaluation test of floating virus control performance, the functional material was produced by using a nonwoven fabric of the aluminum fiber with a fiber thickness of 50 [μm] as the aluminum base material and directly subjecting this aluminum base material to a zinc phosphate chemical conversion treatment in the same procedure as in Example 4 as described above, without the zinc plating treatment shown in FIG. 2 and designated as Example 8. Since the functional material of Example 8 forms the functional film in the same procedure as that of Example 4, the interval between the protrusions formed on the functional film of Example 8, the area of the recess, and the average area of the recess are each approximately the same as those of Example 4.

<Floating Virus Suppression Performance Evaluation Test>

First, the configuration of a test apparatus 5 used to conduct the floating virus suppression performance evaluation test will be described with reference to FIGS. 6A and 6B.

Figure 6A:
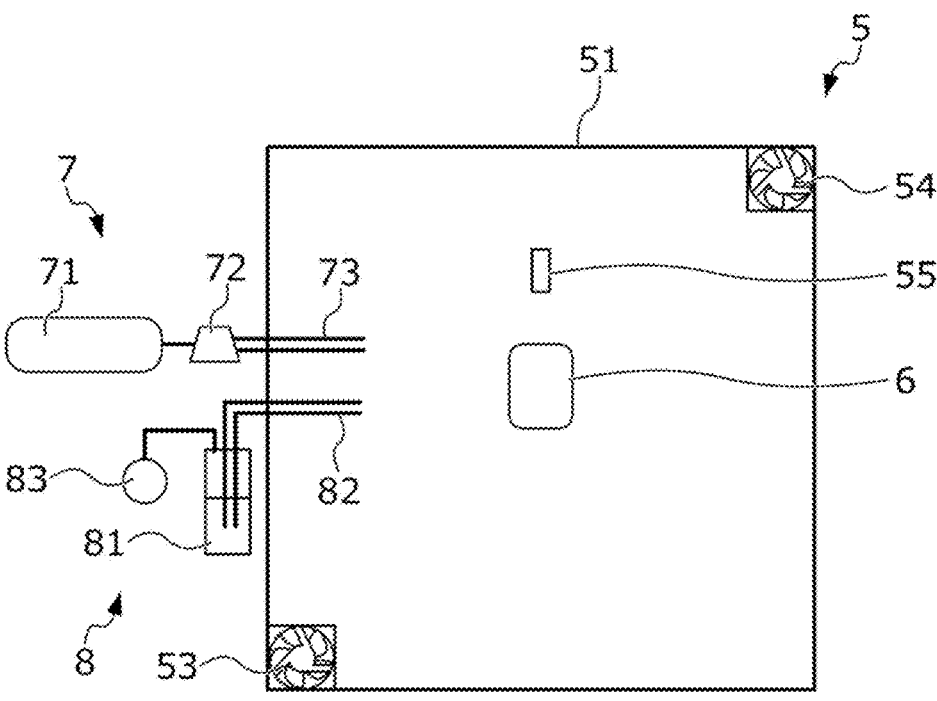
FIG. 6A is a plan view of a test apparatus used to conduct a floating virus suppression performance evaluation test.
Figure 6B:
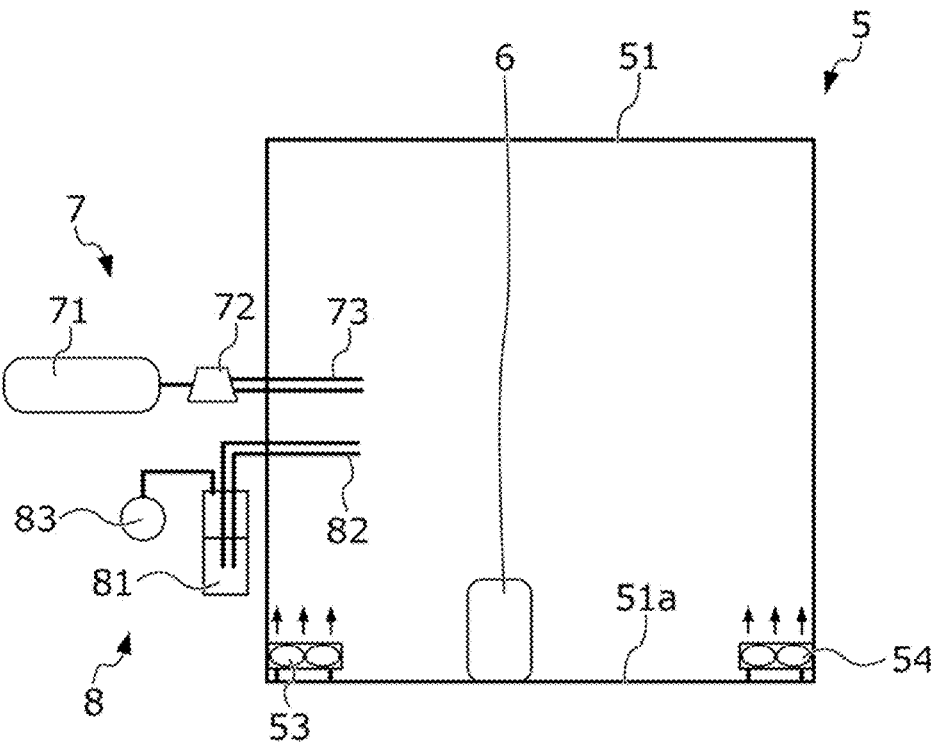
FIG. 6B is a side view of a test apparatus used to conduct a floating virus suppression performance evaluation test.

FIG. 6A is a plan view of the test apparatus 5 used to conduct the floating virus suppression performance evaluation test, and FIG. 6B is a side view of the test apparatus 5.

The test apparatus 5 is equipped with a box-shaped test chamber 51, a test article 6, two agitating fans 53 and 54 and a thermometer/hygrometer 55 provided in this test chamber 51, a virus sprayer 7 that sprays virus solution into the test chamber 51, and a virus collector 8 that collects viruses floating in the test chamber 51. In the floating virus suppression performance evaluation test, the performance of the functional material in suppressing floating viruses was evaluated by running the test sample 6, which was created by attaching the functional material to the air flow path inside a commercially available air purifier (IG-HCF15, manufactured by SHARP CORPORATION), in the test chamber 51 where viruses were floating.

The test chamber 51 used was cubic and had one side of 1 [m]. The test sample 6 was placed in the substantial center of the bottom 52a of the test chamber 51.

Figure 7:
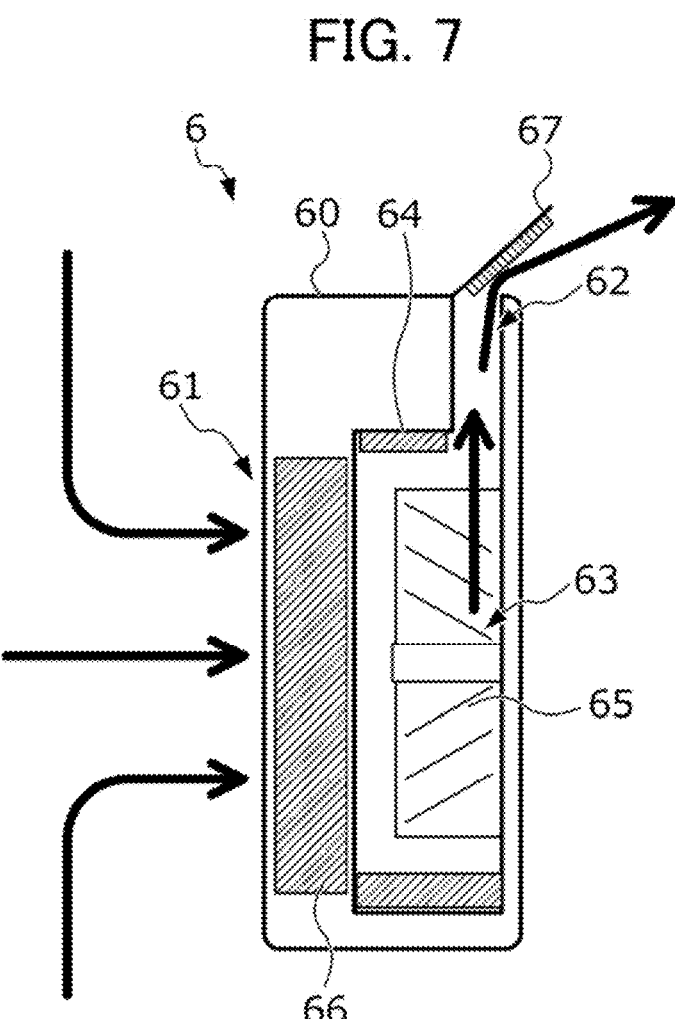
FIG. 7 is a cross-sectional view of a test sample.

FIG. 7 is a cross-sectional view of the test sample 6. The test sample 6 is equipped with a rectangular-shaped housing 60, a sirocco fan 63 that sucks the air from an inlet 61 provided on the front side of the housing 60 and discharges it from an air outlet 62 provided on the upper side of the housing 60, a flat filter section 66 provided between the inlet 61 and the sirocco fan 63, and a louver 67 provided at an air outlet 62. The sirocco fan 63 has a scroll-type casing 64 and a multi-blade centrifugal fan 65 freely rotatable in the casing 64. In such a test sample 6, air taken into the housing 60 from the inlet 61 by rotating the fan 65 passes through the filter section 66, then flows along the inner wall of the casing 64, and is discharged along the louver 67 to the outside of the housing 60.

In the floating virus suppression performance evaluation test, this filter-like functional material according to the present embodiment was installed in the part of the test sample 6 that serves as the airflow path. More specifically, the functional materials were installed in portions shown in hatching in FIG. 7, i.e., at three locations in the test sample 6: the filter section 66, the inner wall of the casing 64 of the sirocco fan 63, and the inner surface of the louver 67. Note that when evaluating the performance of the functional materials of Example 7, two layers of the functional materials were placed on top of each other in the filter section 66.

Back to FIGS. 6A and 6B, the two agitating fans 53 and 54 are located in the corners of the bottom 52a, with the test sample 6 sandwiched between them. The two agitating fans 53 and 54 agitate the air in the test chamber 51 by blowing the air taken in from the bottom 52a side upward.

The thermometer/hygrometer 55 measures the temperature and humidity in the test chamber 51, more specifically, the temperature and humidity on the bottom 52a side of the test chamber 51.

The virus sprayer 7 is equipped with a compressor 71 that generates compressed air, a nebulizer 72 that stores pre-prepared virus solution, and a nozzle 73 that is provided through the side 52b of the test chamber 51. The nebulizer 72 atomizes the virus solution using compressed air supplied from the compressor 71 and sprays the atomized virus solution into the test chamber 51 via the nozzle 73. As illustrated in FIGS. 6A and 6B, the virus sprayer 7 sprays the atomized virus solution slightly above the test sample 6 in the test chamber 51.

The virus collector 8 is equipped with an impinger 81 that stores the virus collection solution, a tube 82 that connects the test chamber 51 and the impinger 81, and a suction pump 83 that sucks air in the impinger 81. When the air in the impinger 81 is sucked by the suction pump 83, viruses floating in the test chamber 51 are sucked into the impinger 81 together with the air and collected by the collection solution.

FIGS. 8A and 8B are the test process charts a and b for the floating virus suppression performance evaluation tests. More specifically, the test process chart a in FIG. 8A shows the procedure for evaluating the natural attenuation of floating viruses, and the test process chart b in FIG. 8B shows the procedure for evaluating the suppression performance of floating viruses by the test sample.

As shown in the test process charts a and b by first, the virus sprayer sprayed the virus solution for 10 minutes while the agitating fans provided in the test chamber were operated, followed by agitation of the test chamber for 2 minutes, and then the virus collector collected the first (0 minute) floating viruses from the air in the test chamber for 2 minutes to measure the number of the floating viruses.

The test virus solution to be sprayed by the virus sprayer 7 contained the test virus *Escherichia coli* phage MS2N BRC 102619 (*Escherichia coli* phage) and the host bacterium *Escherichia coli* NBRC 106373 (*Escherichia coli*), and the test virus was cultured in the host bacteria solution and then used. More specifically, the test virus was inoculated into the host bacterial solution cultured overnight at 36±2° C. in Nutrient Broth (Difco), mixed with semi-fluid agar, and layered on regular agar medium (Nissui). Here, the semi-fluid agar used was prepared by mixing Nutrient Broth, 0.5% sodium chloride (Wako, special grade, for physiological saline), and 0.5% Agar (Difco). After culturing at 36±2° C. for 18 hours, the host bacteria were centrifuged off and filtered through a membrane filter (Bottle-top filter, TPP) with a pore diameter of 0.22 μm to obtain a test virus solution of approximately $10^{11}$ PFU/mL. This was further diluted 100-fold in a ⅒ NB medium and used for testing.

The virus solution was sprayed using the virus sprayer 7 in the following procedure. More specifically, compressed air was supplied from the compressor to the nebulizer containing the virus solution, and the virus solution was sprayed into the test chamber at about 0.2 mL per minute for 10 minutes to float. The air pressure discharged from the compressor was 1.5 kg/cm², and the volume of air discharged was 7.0 L/min.

The floating viruses were collected using the virus collector 8 in the following procedure. More specifically, 20 mL of phosphate-buffered saline to which 0.015% sodium thiosulfate (Wako, first grade) was added was placed in the impinger as the collection solution. For each collection, the air in the test chamber was sucked at 10 L per minute for 2 minutes by the suction pump to collect the floating viruses in the test chamber.

The number of the floating viruses was measured in the following procedure. More specifically, the collection solution in the impinger after the collection of the floating viruses and a recovered solution of adherent viruses were used as a sample stock solution, and a 10-fold dilution series was prepared with phosphate-buffered saline. The sample stock solution and diluted solution were mixed with the host bacteria on the semi-fluid agar and layered on the regular agar medium. After culturing at 36±2° C. for 17 to 21 hours, the generated plaques were counted to determine the number of the floating viruses per 20 L of air.

In the test process chart a, floating viruses were collected from the air in the test chamber by the virus collector for 2 minutes each time a predetermined time (15, 30, 45, 60, 90, and 180 minutes) elapsed from the collection of the first floating virus until 180 minutes elapsed, and the number of the floating viruses was measured. In the test process chart b, floating viruses were collected from the air in the test chamber by the virus collector for 2 minutes each time a predetermined time (15, 30, 45, 60, 90, and 180 minutes) elapsed from the collection of the first floating virus while running the test sample until 180 minutes elapsed, and the number of the floating viruses was measured. As mentioned above, a commercially available air purifier Was used as the test sample, but the ion generation function of this air purifier was turned off and only the air blowing function was turned on in the floating virus suppression performance evaluation test. At this point, the airflow rate was set at 0.54 m³/min.

Figure 9:
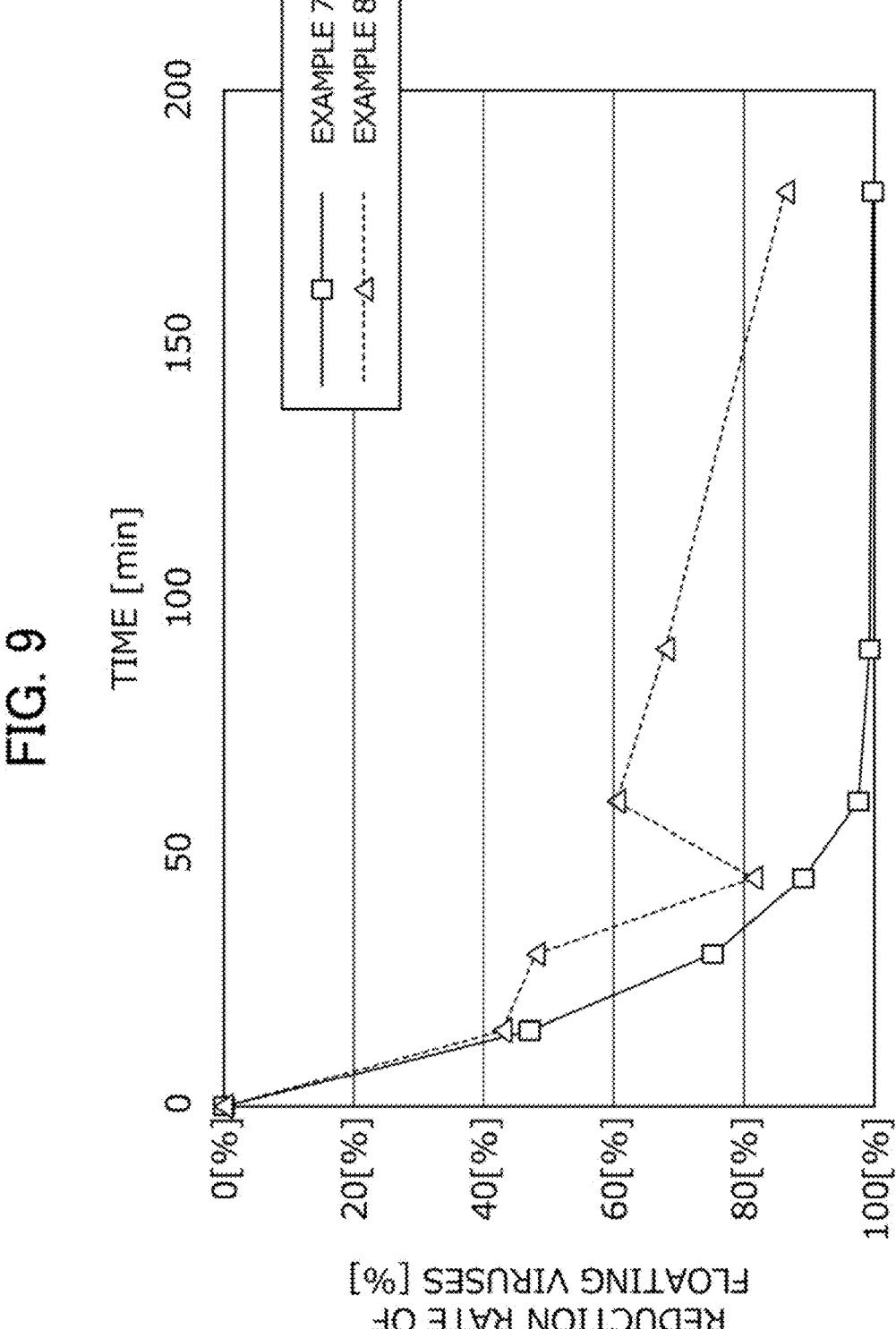
FIG. 9 is a graph showing a change in a reduction rate of floating viruses at each time by a test sample with a functional material of Example 7 and a test product with a functional material of Example 8.

FIG. 9 is a graph showing a change in a reduction rate [%] of floating viruses at each time by a test sample with the functional material of Example 7 and a test sample with a functional material of Example 8. The reduction rate of the floating viruses at each time point was calculated by the following equation (1).

[Expression 1]

$$\text{Reduction rate } [\%] = \left(1 - \frac{1}{10^{\textit{Net logarithmic reduction value}}}\right) \qquad (1)$$

TABLE 1

| | REDUCTION RATE OF FLOATING VIRUS PER HOUR [%] | | | | | |
|---|---|---|---|---|---|---|
| | 15 MIN | 30 MIN | 45 MIN | 60 MIN | 90 MIN | 180 MIN |
| EXAM-PLE 7 | 47.1 | 75.2 | 89.1 | 97.6 | 99.3 | 99.8 |
| EXAM-PLE 8 | 42.9 | 48.0 | 81.4 | 60.4 | 67.9 | 86.3 |

In the above equation (1), the logarithmic reduction value was defined by the following equation (2), and the net logarithmic reduction value was defined by the following equation (3).

Logarithmic reduction value=Log₁₀(the number of first viruses/the number of viruses per elapsed time)    (2)

Net logarithmic reduction value=Logarithmic reduction value during operation of the test sample (measured value in the test process chart b)−Logarithmic reduction value upon stopping test sample (measured value in the test process chart a)    (3)

As shown in FIG. 9 and Table 1, the test sample with the functional material according to Example 8 had a floating virus reduction rate of less than 99 [%] within 180 minutes, thus failing to confirm its superior floating virus suppression performance could not be confirmed, whereas the test sample with the functional material according to Example 7 had a floating virus reduction rate of 99 [%] or more within 180 minutes, thus confirming its superior floating virus suppression performance. Therefore, it was verified that the functional material of Example 7 has a particularly stronger antiviral action than the functional material of Examples 8. Note that the interval between the protrusions formed on the functional film of the functional materials of Examples 7 and 8, the area of the recess, and the average area of the recess are each approximately the same as those of the functional materials of Examples 3 and 4. Therefore, the functional materials of Examples 7 and 8 have the same antifungal effect and bactericidal effect as those of Examples 3 and 4.

Third Embodiment

Next, a functional material and a method for producing the same according to the third embodiment of the present invention will be described with reference to the drawings.

The shape of the functional material according to the present embodiment differs from that of the functional material of the first embodiment described with reference to FIG. 1 or the like. That is, the shape of the functional material 1 according to the first embodiment is flat, while the shape of the functional material according to the present embodiment is mesh and can be used as a filter. More specifically, the first embodiment describes a case in which the functional material 1 is a flat metal substrate 2 with a functional film 3, a zinc phosphate film, formed on it's surface. In contrast, the present embodiment differs from the first embodiment in terms of using a mesh-shaped metal base material, more specifically, aluminum mesh, as the metal base material and forming a functional film on the surface of this metal base material. Note that a specific procedure for the zinc phosphate chemical conversion treatment to form a functional film (i.e., a zinc phosphate film with numerous micron-order recesses and protrusions in fine and irregular shapes) on the surface of such a mesh-shaped metal base material is the same as in the first embodiment, so a detailed description will be omitted.

The functional film, a zinc phosphate film formed on the surface of the fibers constituting the functional material as described below, has an antifungal effect, a bactericidal effect, and an antiviral action as in the second embodiment.

Next, the contents of antiviral tests conducted to verify the antiviral action of the mesh-shaped functional materials according to the present embodiment and Examples 9 and 10 will be described.

<Example 9>

In the above antiviral tests, an aluminum base material was prepared by using A5056 processed into a mesh shape with a density of 30 mesh per inch, and then a functional material was produced by directly subjecting this aluminum base material to a zinc phosphate chemical conversion treatment in the same procedure as Example 3 as described above without applying the zinc plating treatment shown in FIG. 2 and designated as Example 9. Note that the aluminum base material had a diameter of 0.25 [μm], a mesh pore diameter of 0.596 [μm], and a pitch of 0.8467 [μm]. Since the functional material of Example 9 forms the functional film in the same procedure as that of Example 3, the interval between the protrusions formed on the functional film of Example 9, the area of the recess, and the average area of the recess are each approximately the same as those of Example 3. Therefore, the interval between the protrusions formed on the functional film of Example 9 is at least in the range of 0.5 [μm] to 1.5 [μm], and the area of the recess is at least in the range of 0.05 [μm] to 2.0 [μm$^2$].

<Example 10>

The functional material of Example 9 was subjected to a thermal load assuming that, for example, it is used as an automobile part, and designated as Example 10. More specifically, the functional material of Example 9 was subjected to high temperature treatment at 80° C. for 36 hours and designated as Example 10.

Antiviral Test

Figure 10:
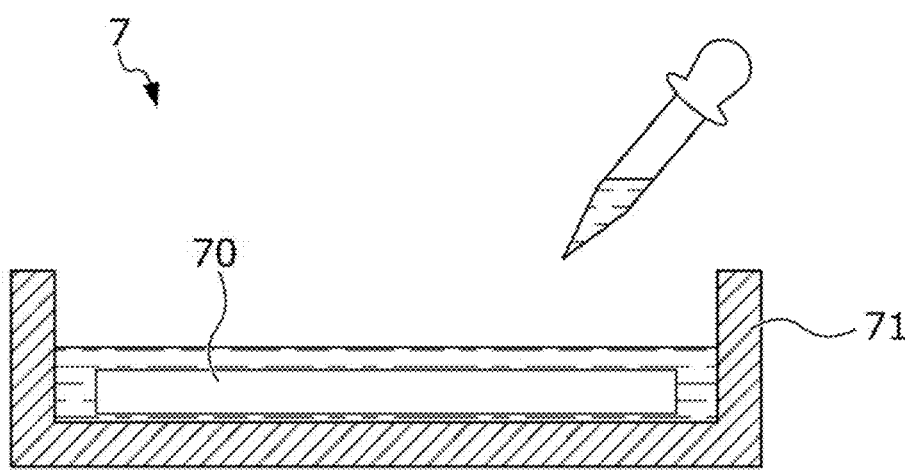
FIG. 10 is a view illustrating a configuration of a test apparatus used in an antiviral test.

In antiviral tests, the function of inactivating viruses was verified for Examples 3, 9, and 10 by using a test apparatus 7 as illustrated in FIG. 10. More specifically, the virus solution containing bacteriophage Qβ was added dropwise to the functional film of a sample 70 placed in a container 71, and the number of viruses after 24 hours was measured by a method referring to JIS 2801 to verify the virus inactivation function of the functional materials of Examples 3, 9, and 10.

Here, the test virus was NBRC 20012 (bacteriophage Qβ), and a test liquid was the test solution diluted in a 1/500 NB medium (10$^6$ [PFU/mL]). After adding 2 [mL] of the test solution obtained as described above so as to cover the entire sample 70, the lid was immediately closed to prevent drying. The samples were then allowed to stand still in a humidification box at a temperature of 25° C. and a humidity of 100 [%] for 24 hours.

After the above treatment, the whole phage solution in the container 71 was recovered, and a SCDLP medium (2 [mL]) was used for co-washing of the bottom of the base material by pipetting. The diluent was further adjusted by adding 16 [mL] of the SCDLP medium (10$^1$ diluent), and if necessary, the recovered solution was diluted with SM buffer (10$^2$ to 10$^6$ diluent). In addition, the infectivity titer [PFU/mL] was calculated for the recovered solution obtained as described above by a known viral plaque method.

Table 2 below is a table listing the results of the antiviral tests. As listed in Table 2 below, the infectivity titer of the virus solution without samples after 24 hours was 1.28×10$^6$ [PFU/mL], whereas the infectivity titer after 24 hours in Example 3, Example 9, and Example 10 were all below the detection limit (0.00).

TABLE 2

| | INFECTIVITY TITER AFTER 24 HOURS [PFU/mL] |
|---|---|
| NO SAMPLE | 1.28 × 10$^6$ |
| EXAMPLE 3 | DETECTION LIMIT (0.00) |
| EXAMPLE 9 | DETECTION LIMIT (0.00) |
| EXAMPLE 10 | DETECTION LIMIT (0.00) |

As described above, it was verified that the functional materials according to Examples 3, 9, and 10 each have an infectivity titer after 24 hours less than the detection limit and a superior antiviral action, and can be used as a virus inactivation material. Since the functional material of Example 10, obtained by applying a thermal load to the functional material of Example 9, also exhibited a superior antiviral action, it was verified that the functional material according to Example 9 is also suitable for things which be used in high-temperature environment, for example, an automobile part. Note that none of the functional films of Examples 3, 9, and 10 peeled off after the antiviral tests. Therefore, it was also verified that the functional films, the zinc phosphate films, in the functional materials of Examples 3, 9, and 10 each have sufficient strength. Note that the interval between the protrusions formed on the functional materials of Examples 9 and 10, the area of the recess, and the average area of the recess are each approximately the same as those of the functional material of Example 3. Therefore, the functional materials of Examples 9 and 10 have the same antifungal effect and bactericidal effect as those of Example 3.

In the above, one embodiment of the present invention is described, but the present invention is not limited thereto. The configurations of the detailed parts may be modified as appropriate within the scope of the gist of the present invention. For example, the above embodiments describe a case in which a product obtained by forming the zinc layer 25 on the surface of the aluminum base material 21 is used as the metal base material 2 of the functional material 1, but the present invention is not limited thereto.

EXPLANATION OF REFERENCE NUMERALS

1 Functional Material
2 Metal Base Material
21 Aluminum Base Material
25 Zinc Layer
3 Functional Film

The invention claimed is:

1. A functional material comprising:
a metal base material, being aluminum or an aluminum alloy based on aluminum, and
a zinc phosphate film directly formed on a surface of the metal base material, wherein
micron-order recesses and protrusions are formed on the zinc phosphate film, and
the zinc phosphate film has at least one selected from an antifungal effect, a bactericidal effect, and an antiviral action.

2. The functional material according to claim 1, wherein an interval between protrusions formed on the zinc phosphate film is in a range of 0.5 to 50.0 μm.

3. The functional material according to claim 2, the interval between protrusions is in a range of 0.5 to 6.0 μm and
the zinc phosphate film has a stronger bactericidal effect than the metal base material.

4. The functional material according to claim 2, wherein the interval between protrusions is in a range of 2.7 to 50.0 μm and
the zinc phosphate film has a stronger antifungal effect than the metal base material.

5. The functional material according to claim 2, wherein the interval between protrusions is in a range of 0.5 to 1.5 μm and the zinc phosphate film has a stronger antiviral action than the metal base material.

6. The functional material according to claim 1, wherein a recess formed on the zinc phosphate film has an area in a range of 0.05 to 1,400 $\mu m^2$.

7. The functional material according to claim 6, wherein the recess has an area in a range of 0.05 to 31.0 $\mu m^2$ and the zinc phosphate film has a stronger bactericidal effect than the metal base material.

8. The functional material according to claim 6, wherein the recess has an area in a range of 0.05 to 2.0 $\mu m^2$ and the zinc phosphate film has a stronger antiviral action than the metal base material.

9. A method for producing a functional material, the method comprising:
   subjecting a metal base material to a zinc phosphate chemical conversion treatment to form a zinc phosphate film having micron-order recesses and protrusions directly on a surface of the metal base material and having at least one selected from an antifungal effect, a bactericidal effect, and an antiviral action, the metal base material being aluminum or an aluminum alloy composed of aluminum as a main component.

10. A functional material comprising:
   a metal base material and
   a zinc phosphate film formed on a surface of the metal base material by subjecting the metal base material to contact with a zinc phosphate treatment solution, wherein micron-order recesses and protrusions are formed on the zinc phosphate film,
an interval between protrusions formed on the zinc phosphate film is in a range of 0.5 to 50 $\mu m$, and
the zinc phosphate film has at least one selected from a stronger antifungal effect than the metal base material, a stronger bactericidal effect than the metal base material, and a stronger antiviral action than the metal base material.

11. The functional material according to claim 1, wherein the zinc phosphate film is directly formed on the surface of the metal base material by performing a surface conditioning process in which the metal base material is immersed in a surface conditioning solution to attach nuclei, and a zinc phosphate conversion treatment in which the zinc phosphate treatment solution is contacted with the metal base material that has undergone the surface conditioning process.

12. The functional material according to claim 10, wherein the zinc phosphate film is formed on the surface of the metal base material by performing a surface conditioning process in which the metal base material is immersed in a surface conditioning solution to attach nuclei, and a zinc phosphate conversion treatment in which the zinc phosphate treatment solution is contacted with the metal base material that has undergone the surface conditioning process.

13. The functional material according to claim 1, wherein the metal base material is a fibrous or a mesh filter.

14. The functional material according to claim 10, wherein the metal base material is a fibrous or a mesh filter.

* * * * *